United States Patent [19]

Yamada et al.

[11] Patent Number: 5,116,573
[45] Date of Patent: May 26, 1992

US005116573A

[54] LABELLED VITAMIN D$_3$ DERIVATIVE AND PRODUCTION PROCESS THEREOF

[75] Inventors: Sachiko Yamada, Hachioji; Koichi Niimura, Sayama; Kenji Fukushima, Yokohama; Yuji Maeda, Nagareyama, all of Japan

[73] Assignee: Kureha Kagaku Kogyo Kabushiki Kaisha, Tokyo, Japan

[21] Appl. No.: 403,466

[22] Filed: Sep. 7, 1989

[30] Foreign Application Priority Data

Sep. 14, 1988 [JP] Japan .................. 63-231339

[51] Int. Cl.$^5$ ............... A61K 43/00; A61K 49/02; A61K 31/59; C07C 13/15
[52] U.S. Cl. ..................... 424/1.1; 552/653; 514/167
[58] Field of Search .......... 424/1.1; 514/167; 568/374; 552/653

[56] References Cited

U.S. PATENT DOCUMENTS 4,898,855  2/1990  Baggiolini et al. ............... 514/167

FOREIGN PATENT DOCUMENTS 190962  10/1984  Japan .................. 568/374

OTHER PUBLICATIONS

Yamada et al., *Steroids*, 54(2), pp. 145–157, Aug. 1989.
Yamada et al., *J. Org. Chem.*, 48(20), 3484–88, 1983.
Yamada et al., *Tetrahedron Letters*, 22(32), pp. 3085–3088, 1981.
Reischl et al., *Helvetica Chimica Acta*, 62(6), pp. 1763–1769, 1979.

*Primary Examiner*—Robert L. Stoll
*Assistant Examiner*—John M. Covert
*Attorney, Agent, or Firm*—Nixon & Vanderhye

[57] ABSTRACT

The present invention discloses a novel, labelled vitamin D$_3$ derivative in which hydrogen atoms on the skeleton portion, i.e. 6- and 19-positions, are substituted with a deuterium atom or a tritium atom, as well as a novel production process of the labelled vitamin D$_3$ derivative carried out by way of sulfur dioxide addition reaction of a vitamin D$_3$ derivative. The labelled portion of the novel vitamin D$_3$ is resistant against in vivo metabolism and make a long period tracing of its pharmacodynamics in a living body possible.

5 Claims, No Drawings

LABELLED VITAMIN D₃ DERIVATIVE AND PRODUCTION PROCESS THEREOF

BACKGROUND OF THE INVENTION

The present invention concerns with a novel labelled vitamin D₃ derivative represented by the formula (I):

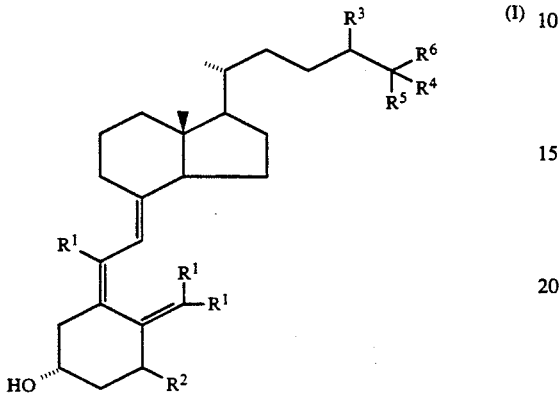

wherein $R^1$ represents a deuterium atom or a tritium atom, $R^2$, $R^3$, and $R^4$ independently represent a hydrogen atom or a hydroxy group and $R^5$ and $R^6$ represent respectively a methyl group, a hydroxymethyl group or a trifluorocarbon group, as well as a production process thereof.

Vitamin D₃ (hereinafter referred to as "VD₃") derivatives have been used as therapeutical medicines for various diseases of bone such as osteoporosis and it is essential to recognize pharmacodynamics of VD₃ derivatives in a living body in order to evaluate their therapeutical effect and safety, as well as to increase an efficiency of the therapy. For this purpose, it is necessary to introduce radioactive isotopes to the VD₃ derivatives by using a chemical or biological method and label the derivatives.

Responding to such requirement, VD₃ derivatives labelled with radioactive isotopes at a side chain by means of a biochemical method have been used so far. [Refer to H. F. DeLuca et al., Journal of Biological Chemistry; vol. 251, p. 397–402(1976)].

However, since the labelled VD₃ derivatives used so far are labelled at side chains and such side chains are prone to be metabolized in vivo metabolism, there has been a fundamental problem that when the labelled VD₃ derivative is administered to a living body, i.e., the labelled side chain is easily removed from its skeleton portion under the effect of in vivo metabolism. Therefore, there has been no remarkable progress in the field to compare the efficacies among various kinds of VD₃ derivatives and to acquire the features of the individual VD₃ derivatives.

The present inventors have studied extensively to overcome the above drawbacks and, as a result, have completed the present invention based on the finding that a VD₃ derivative having a radio isotope at the skeleton portion can possess a stable labelled performance in a living body and have established a novel process to produce the labelled derivatives.

SUMMARY OF THE INVENTION

An object of the present invention is to provide a novel VD₃ derivative represented by the formula (I):

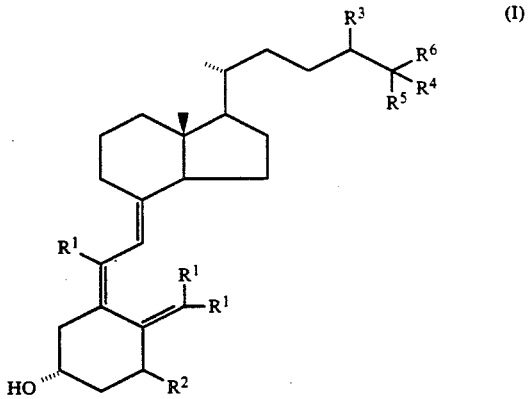

wherein $R^1$ represents a deuterium atom or a tritium atom, $R^2$, $R^3$ and $R^4$ independently represent a hydrogen atom or a hydroxy group and $R^5$ and $R^6$ represent respectively a methyl group, a hydroxymethyl group or a trifluorocarbon group, as well as a production process thereof.

Another object of the present invention is to provide a novel VD₃ derivative capable of stably keeping a performance as a labelled compound in a living body.

Further object of the present invention is to provide a novel process for producing a VD₃ derivative represented by the above formula (I) based on a novel finding that an SO₂ adduct of a known VD₃ derivative has active hydrogen atoms on its skeleton portion which can be replaced easily by deuterium atoms or tritium atoms.

DETAILED DESCRIPTION OF THE INVENTION

The present invention describes a VD₃ derivative represented by the formula (I):

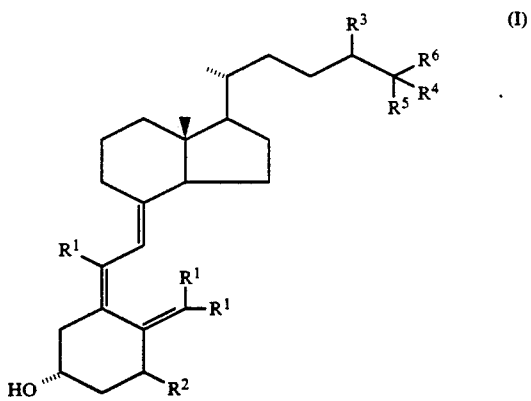

wherein $R^1$ represents a deuterium atom or a tritium atom, $R^2$, $R^3$ and $R^4$ independently represent a hydrogen atom or a hydroxy group and $R^5$ and $R^6$ represent respectively a methyl group, a hydroxymethyl group or a trifluorocarbon group, (hereinafter $R^1$, $R^2$, $R^3$, $R^4$, $R^5$ and $R^6$ in the formulae of the VD₃ derivatives in the present specification have the same meanings as described above), as well as a production process thereof.

The present invention is based on a finding that sulfur dioxide adduct of a VD₃ derivative can have active hydrogen atoms on its skeleton portion and the activated hydrogen atoms can be replaced quite easily by a labeling element, that is a deuterium atom or a tritium atom.

According to the present invention, it is possible to label 6- and 19-positions of a VD₃ derivative [refer to the following formula (I) having position-indicating numbers] selectively with a deuterium atom or tritium atom and, since the labelled portion of VD₃ is the skeleton, it has now become possible to trace the VD₃ easily in a living body irrespective of in vivo metabolism on the side chain.

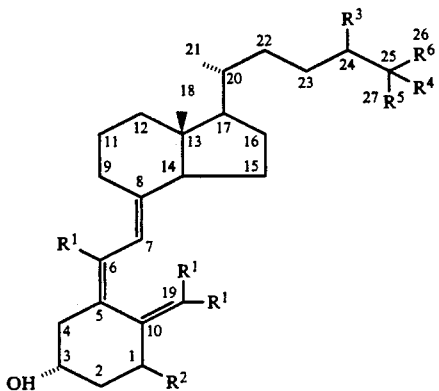

The compound (II) as the starting material of the substance according to the present invention can be exemplified as follows:

24,25-dihydroxycholecalciferol: [24,25-(OH)₂-VD₃],
24R,25-dihydroxycholecalciferol: [24R,25-(OH)₂-VD₃],
24S,25-dihydroxycholecalciferol: [24S,25-(OH)₂-VD₃],
25,26-dihydroxycholecalciferol: [25,26-(OH)₂-VD₃],
1α,25-dihydroxycholecalciferol: [1α,25-(OH)₂-VD₃],
1α,24-dihydroxycholecalciferol: [1α,24-(OH)₂-VD₃],
1α,24,25-trihydroxycholecalciferol: [1α,24,25-(OH)₃-VD₃],
25-hydroxycholecalciferol: [25-(OH)-VD₃],
1α-hydroxycholecalciferol: [1α-(OH)-VD₃], and
24-hydroxycholecalciferol: [24-(OH)-VD₃].

Hereafter, synthetic method of the derivatives is described.

Three hydrogen atoms at 6- and 19-positions in the formula (II) are activated under the effect of SO₂ and the sulfur dioxide adducts can easily release proton to produce carbanions.

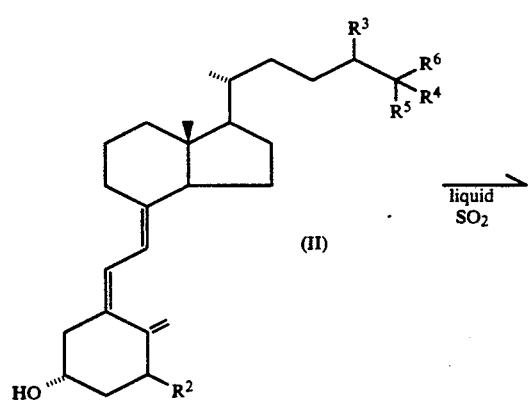

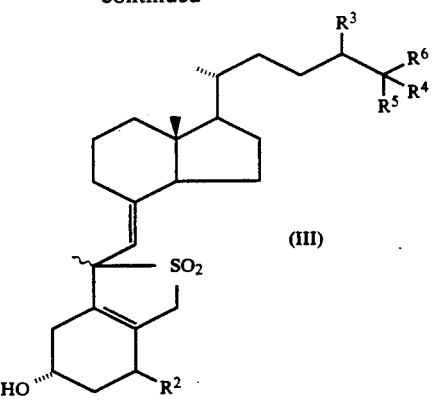

As a matter of fact, it was possible for a deuterium or tritium water to react with the compound represented by the formula (III) and replace the hydrogen atoms at 6- and 19- positions with deuterium atoms or tritium atoms.

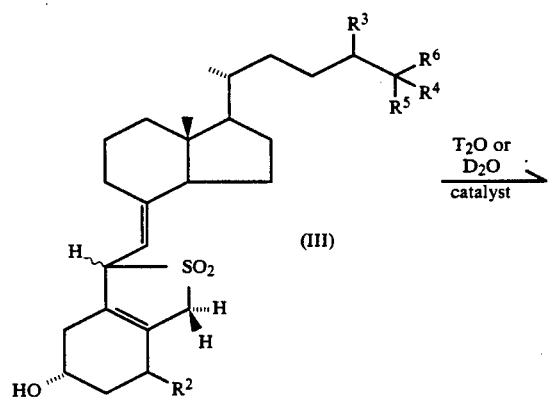

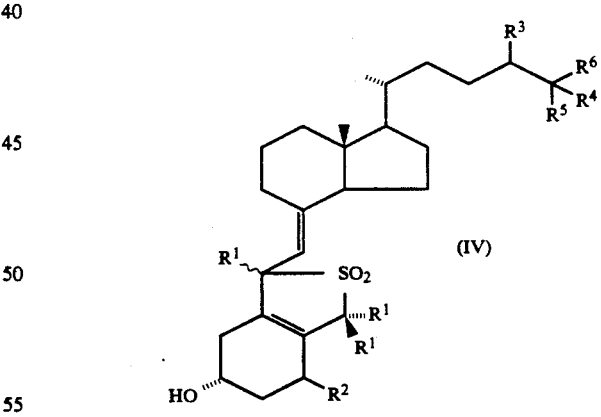

In detail, D₂O or T₂O was added to a compound represented by the formula (III) in a solvent under the presence of a base catalyst such as t-butoxy potassium (t-BuOK) or NaOCH₃, reacted at −50° to 40° C. for 0.5 to 5 hours and obtained a compound represented by the formula (IV).

Then, a thermolytic desulfonylation was carried out at a temperature of 0° to 150° C. and a compound having a original skeleton was obtained. However, since the compound contains an isomer, they are separated from each other to obtain a compound represented by the formula (I) and a compound represented by the formula (V). Then, by photoisomerizing the compound represented by the formula (V) and/or the desulfonylation product as it was, the compound according to the present invention represented by the formula (I) was obtained.

After the reaction was over, the resultant compound was purified by a usual method of purifying such kind of compound, for an example, a silica gel column chromatography.

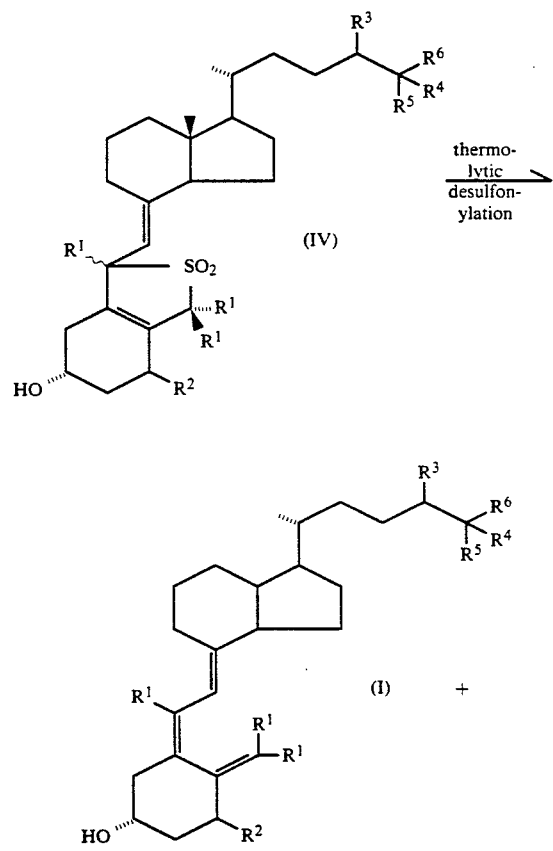

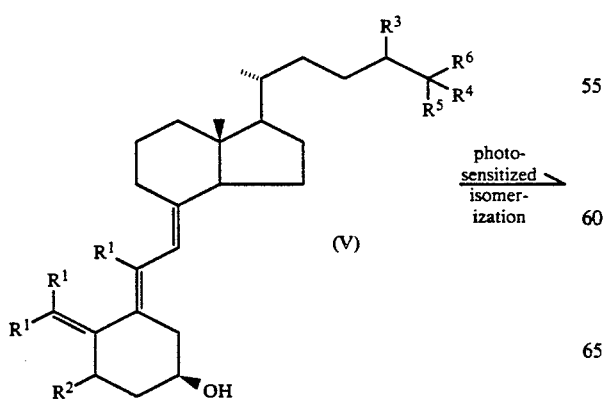

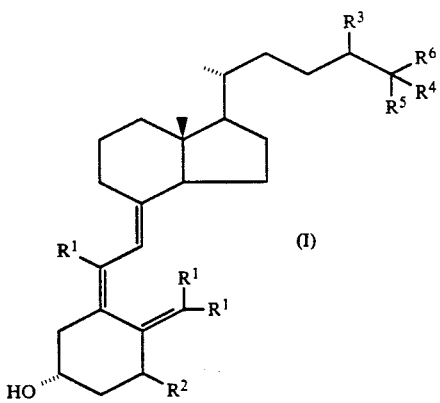

Since a VD$_3$ derivative labelled on a side chain undergoes metabolism when administered in a living body and the labelled portion is easily removed from the skeleton, for example, 24,25-(OH)$_2$-[23,24(n)-T]-VD$_3$ loses its side chain to form 23-(OH)-24,25,26,27-tetranol-VD$_3$, such labelled VD$_3$ derivative is difficult to be detected in a living body as a radioisotope.

On the other hand, since the substance of the present invention is labelled on its skeleton, even when administered and faced in vivo metabolism and its side chain is removed from the skeleton, the reduction of radioactivity is quite small. For instance, when 24R,25-(OH)$_2$-(6,19,19-D)-VD$_3$ is administered, it forms 23-(OH)-24,25,26,27-tetranol-(6,19,19-D)-VD$_3$ and the effect of in vivo metabolism on its radioactivity is close to nothing.

The present invention is to be described more specifically referring to the following examples but the scope of the present invention shall not be limited by these examples.

EXAMPLE 1

Production Process for Deuterium Labelled Compound (I') from 24R,25-(OH)$_2$-VD$_3$[Compound (II')].

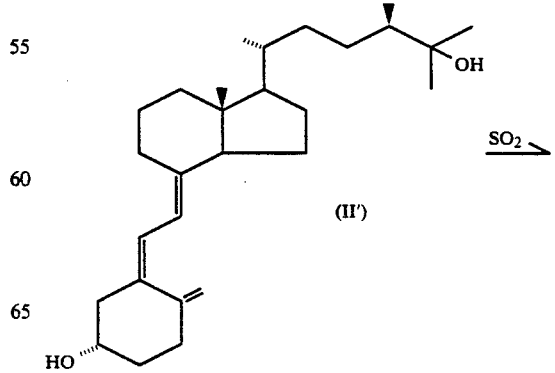

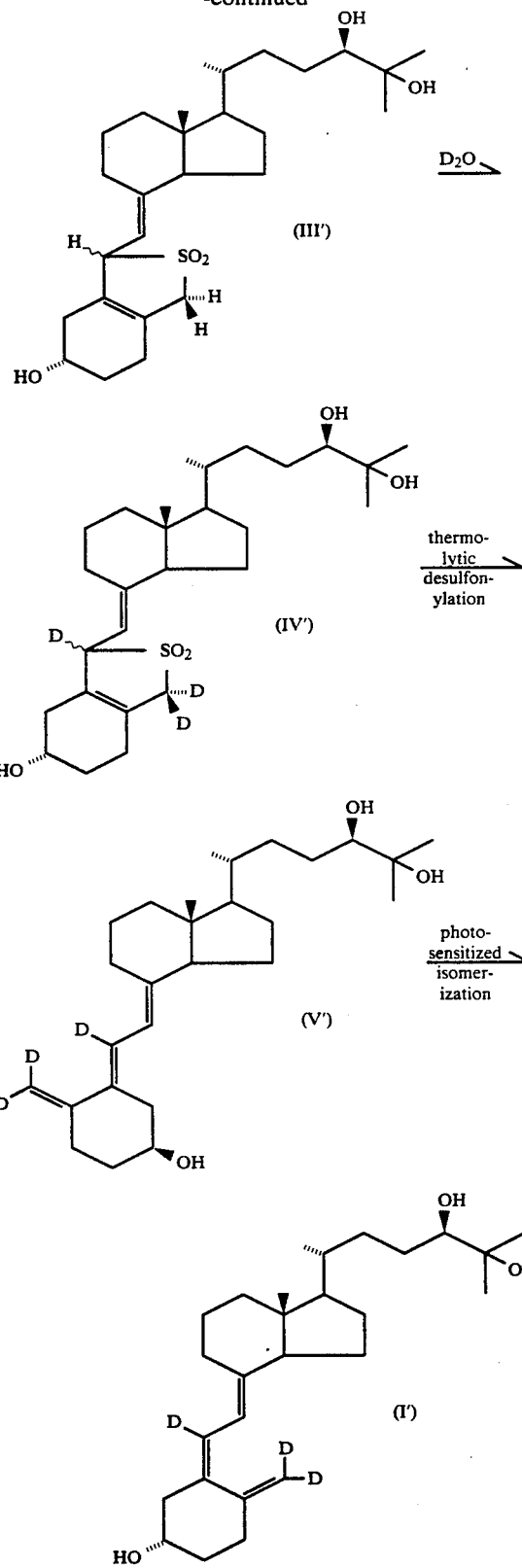

stand. The reaction solution was initially turned yellow but gradually discolored to colorless. After confirming that the reaction solution became colorless and transparent, excess $SO_2$ was distilled off by a suction pump. The residue was purified on silica gel chromatography (5 g, ethyl acetate), to obtain 27.3 mg of compound (III'). (Yield: 97.0%). The product has the following physical properties.

MS (m/e): 416($M^+SO_2$), 398($M^+$—$SO_2$—$H_2O$), and 380($M^+$—$SO_2$—$2H_2O$).

$^1$H-NMR(CDCl$_3$): $\delta$3.33 (1H, m, H-24), $\delta$3.64 (2H, m, H-19), $\delta$4.05(1H,m, H-3), and $\delta$4.70(2H,m, H-6, H-7).

IR (KBr): 3500, 1310, and 1150 cm$^{-1}$.

Elementary analysis (%): Theoretical: C:65.0; H:9.1 Analyzed: C:65.0; H:9.0

(2) Synthesis of Compound (IV')

26 mg (0.052 mmol) of compound (III') was dissolved into 200 μl of dimethylformamide and stirred under an argon gas stream. 50 μl of $D_2O$ was added and then 37.9 mg of t-BuOK suspended in 50 μl of dimethylformamide was added. After reacted at 25° C. for one hour, water was added and extracted with ethyl acetate. After washing the organic layer with an aqueous saturated solution of sodium chloride, the layer was dried on sodium sulfate. After filtration, the solvent was distilled off from the layer, the residue was purified on silica gel column chromatography (5 g, 1% methanol/ethyl acetate), and 25.9 mg of compound (IV') were obtained. (Yield: 99.6%). The product has the following physical properties.

MS (m/e): 419($M^+$—$SO_2$), 401($M^+$—$SO_2$—$H_2O$), and 383($M^+$—$SO_2$—$2H_2O$).

$^1$H-NMR(CDCl$_3$): $\delta$0.58, 0.65 (3H, s, H-18), $\delta$3.32(1H, m, H-24), $\delta$4.08(1H, m, H-3), and $\delta$4.74(1H, m, H-7).

Peaks indicated at $\delta$ 4.70 (H-6) and $\delta$3.64 (H-19) in the compound (III') were disappeared in the compound (IV') and this indicates that the portion (H-6, H-19) were substituted with deuterium atoms.

IR(KBr): 3500, 1305, and 1145 cm$^{-1}$.

(3) Synthesis of Compound (V')

50 μl of DMF was added to a mixture of 10 mg (0.021 mmol) of the compound (IV') and 5 mg of NaHCO$_3$ in a tube and after sealing, the tube was shaken and stirred at 90° C. After one hour, water was added and extracted with ethyl acetate. The organic layer was washed with an aqueous saturated solution of sodium chloride and dried with magnesium sulfate. After filtration, the solvent was distilled off from the layer, the residue was purified on column chromatography (SiO$_2$, 2 g 50% n-hexane/ethyl acetate) and 7.5 mg of compound (V') were obtained. (Yield: 86.5%).

The product had the following physical properties.

MS (m/e): 419 ($M^+$), 401 ($M^+$—$H_2O$), and 383 ($M^+$—$2H_2O$).

$^1$H-NMR (CDCl$_3$): $\delta$0.57, (3H, s, H-18), $\delta$3.32 (1H, m, H-24), $\delta$3.84 (1H, m, H-3), and $\delta$5.86 (1H, s, H-7).

IR(KBr): 3450 cm$^{-1}$.

UV(EtOH): $\lambda_{max}$273 nm.

(4) Synthesis of Compound (I')

(1) Synthesis of Compound (III')

24.4 mg (0.0587 mmol) of compound (II') was charged into an egg plant type flask and about 1 ml of $SO_2$ liquefied with cold finger was added and allowed to 7.5 mg of Compound (V') was dissolved into 10 ml of ethanol (95%), 2 mg of Eosin Y was added and irradiated with a halogen lamp (JCV 100–200 GS, manufactured by USHIO Co.) under an argon gas stream. Samples of the reaction solution were analyzed by HPLC (high pressure liquid chromatography) (μ Bondsphere 5μ Si-100A 3.9 mm×15 cm. 10% isopropanol/n-hexane) time to time to observe the reaction. After 5 minutes, the irradiation was stopped and the reaction solution was distilled to remove the solvent, the obtained residue was purified on column chromatography (silica gel 10 g, 50% n-hexane/ethyl acetate) and 7.2 mg of the product were obtained.

Since the product contained a small amount of unreacted compound (V'), compound (I') was separated and purified by HPLC (μ Bondsphere 5μ Si-100A 19 mm×15 cm 7% isopropanol;n-hexane) and obtained 5.5 mg of the compound (I').

(Yield: 74%).

The product has the following physical properties.

MS(m/e): 419 (M+), 401 (M+—H$_2$O), and 383 (M+—2H$_2$O), 274, 256, 145, 139, 121.

The value 274 in MS (m/e) indicates a fragment which is a side chain released from the whole structure. Since the fragment appears at 271 when it is not substituted with deuterium, this indicates that the skeleton portion was substituted with deuterium.

$^1$H-NMR(CDCl$_3$): δ0.55, (3H,s,H-18), δ3.31 (1H,m,H-24), δ3.93 (1H,m,H-3), and δ6.02 (1H,s,H-7).

UV (EtOH): λ$_{max}$ 265 nm.

EXAMPLE 2

Synthesis of Tritium Labelled Compound [Compound (I″)] of 24R,25-(OH)$_2$-VD$_3$ [Compound(II′)].

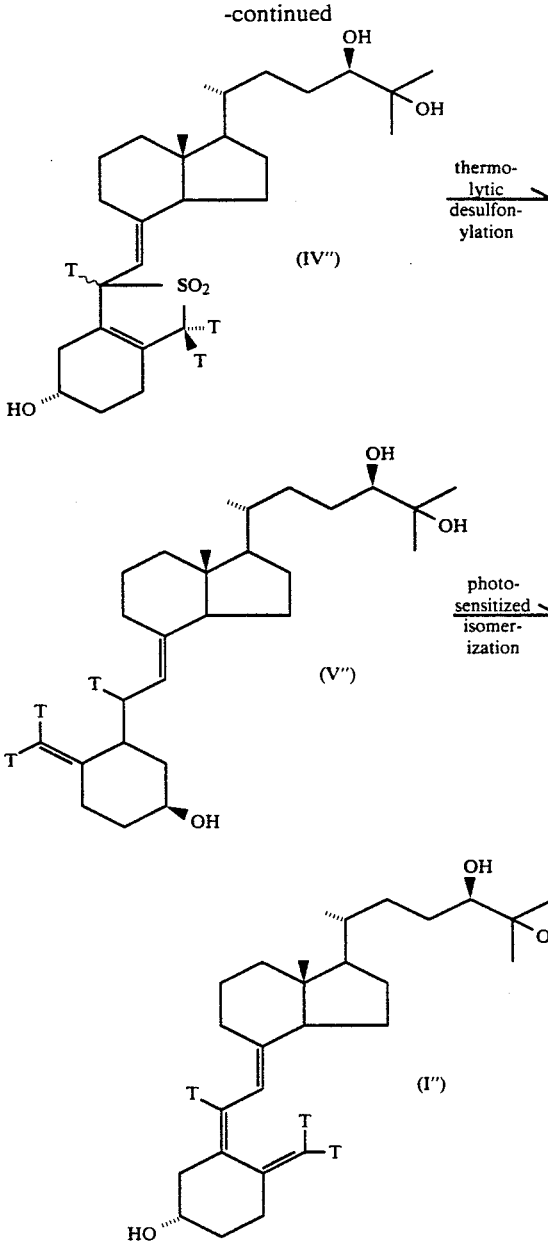

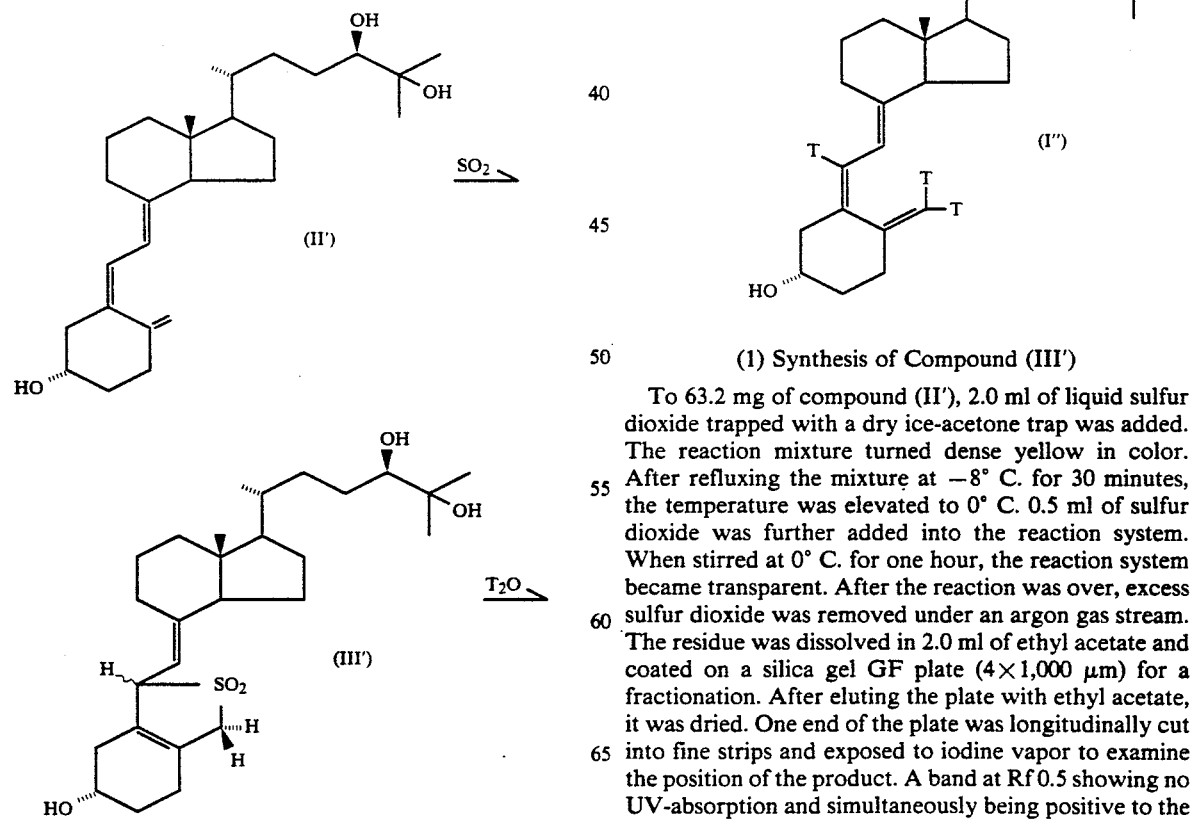

(1) Synthesis of Compound (III')

To 63.2 mg of compound (II'), 2.0 ml of liquid sulfur dioxide trapped with a dry ice-acetone trap was added. The reaction mixture turned dense yellow in color. After refluxing the mixture at −8° C. for 30 minutes, the temperature was elevated to 0° C. 0.5 ml of sulfur dioxide was further added into the reaction system. When stirred at 0° C. for one hour, the reaction system became transparent. After the reaction was over, excess sulfur dioxide was removed under an argon gas stream. The residue was dissolved in 2.0 ml of ethyl acetate and coated on a silica gel GF plate (4×1,000 μm) for a fractionation. After eluting the plate with ethyl acetate, it was dried. One end of the plate was longitudinally cut into fine strips and exposed to iodine vapor to examine the position of the product. A band at Rf 0.5 showing no UV-absorption and simultaneously being positive to the iodine vapor was collected. The starting material was found at Rf 0.85. The fractionated silica gel was extracted with 50 ml of ethyl acetate:methanol (1:1). After filtration, the extract was condensed under a reduced pressure to obtain a white solid.

The product had the following physical properties.

MS (m/e): 416 (M$^+$—SO$_2$), 398 (M$^+$—SO$_2$—H$_2$O), and 380 (M$^+$—SO$_2$—2H$_2$O).

$^1$H-NMR(CDCl$_3$): $\delta$3.33 (1H,m,H-24), $\delta$3.64 (2H,m,H-19), $\delta$4.05 (1H,m,H-3), and $\delta$4.70 (2H,m,H-6, H-7).

(2) Synthesis of Compound (IV")

28 mg of compound (III') was dissolved into 2.0 ml of DMF. When 9.8 mg (0.084 mmol) of t-BuOK was added, it was immediately colored yellow. 50 Ci of tritium water was added to the reaction vessel and stirred after being warmed to a room temperature. 10 ml of an aqueous saturated solution of sodium chloride was added to the reaction product substituted with tritium and extracted with ethyl acetate. The organic layer obtained was washed with an aqueous saturated solution of sodium chloride and dried with sodium sulfate. After removing the drying agent by filtration, the filtrate was dried to be a solid. The residue was dissolved in methanol and then again dried to be a solid. The procedures were repeated twice to remove active tritium water. The compound (IV") has the following physical properties.

MS (m/e): 422 (M$^+$—SO$_2$), 404 (M$^+$—SO$_2$—H$_2$O), and 386 (M$^+$—SO$_2$—2H$_2$O).

(3) Synthesis of Compound (V")

27 mg of compound (IV") was dissolved into a mixed solvent of petroleum ether and ethyl acetate. The total radioactivity was 3.5 Ci. As a result of silica gel TLC (thin layer chromatography) analysis using ethyl acetate as an developing solution, a main band was present at an Rf value lower than that of the starting material. The mixture was heated to 110° C. under an argon gas stream. After 3.5 hours, the solvent was distilled off and the residue was dissolved into 25 ml of ethanol. As a result of TLC analysis, a small amount (not higher than 5%) of the compound was recognized near a spot of the starting material. 130 mg of sodium hydrogen carbonate was added to an ethanol solution and heated under an argon gas stream at 95° C. for 2 hours. After cooling, analysis was conducted and found no change. The reaction mixture subjected to hot de-SO$_2$ was concentrated under a reduced pressure and 2.5 ml of ethyl acetate and 25 ml of distilled water were added. An organic layer was separated from the mixture, washed with 25 ml of distilled water and then dried with sodium sulfate. After filtration, it was concentrated under a reduced pressure. The product had the following physical properties.

MS (m/e): 422 (M$^+$), 404 (M$^+$—H$_2$O), and 386 (M$^+$—2H$_2$O).

(4) Synthesis of Compound (I")

1 mg of compound (V") was dissolved into 25 ml of ethanol. After adding 5 mg of Eosin Y, it was irradiated by a halogen lamp of 300 W in an argon gas stream at a distance of 25 cm for 10 minutes. When the reaction mixture was analyzed by TLC, 1 to 2% of the compound (I") was recognized. The photoreaction mixture was concentrated to 1 ml under a reduced pressure. After charging the concentrated mixture to a TLC plate (3×1,000 μm silica gel GF), it was separated by a developing solution of chloroform:acetone (4:1). A portion having a similar UV activity of a standard product of the compound (II') was collected and extracted with 30 ml of ethanol. After removing silica gel by filtration, a substance having 185 mCi was obtained and by a TLC analysis a tritium compound in the substance was 20 to 30%. The substance was further purified by Hichrom cyano column (25 cm×4.6 mm) using a mixture of n-hexane, isopropanol and water in a weight ratio of 475:25:0.5 as a solvent in a flow rate of 1 ml/minute and monitored with a UV absorption at 260 nm. An eluate showing the same column retention time as that of the standard product was collected. The fraction showed 60 mCi.

The compound (I") purified by HPLC has a radiochemical purity of 80%. The compound obtained by the above procedures was further purified by a Hichrom cyano column of isooctane:isopropanol:methanol (960:40:20). Fractions which had main peaks were collected and dried to be a solid under a reduced pressure. The compound (I") having 31 mCi with 98% purity was obtained in total.

The specific radioactivity of the compound was 54 Ci/mmol based on the value of the UV absorption at 265 nm, and was strong enough in its radioactivity to proceed experiment. It has been found that the labelled tritium in the compound are correctly at 6- and 19-positions by the measurement of mass spectrum.

MS (M/e): 422 (M$^+$), 404 (M$^+$—H$_2$O) 386 (M$^+$—2H$_2$O), 277 (M$^+$—side chain), and 145 (side chain).

The value 277 of MS (m/e) shows the fragment of side chain which is released from the whole structure. Since the fragment exhibit a peak at 271 when it is not substituted with tritium, this indicates that the skeleton portion is substituted with tritium atoms.

UV (EtOH): λmax. 265 nm.

EXAMPLE 3

When the deuterium substitution reaction was performed in the same manners as in Example 1 except for using 1α, 25-(OH)$_2$-VD$_3$ and 25, 26-(OH)$_2$-VD$_3$ instead of 24R, 25-(OH)$_2$-VD$_3$, corresponding substance for each VD$_3$ was obtained. Physical properties of the final product substituted with deuterium atoms are shown below:

1α, 25-(OH)$_2$-(6, 19, 19-D)-VD$_3$:

MS (m/e): 419 (M$^+$), 401 (M$^+$—H$_2$O), and 383 (M$^+$—2H$_2$O).

UV (EtOH): λmax 265 nm.

25, 26(OH)$_2$-(6, 19, 19-D)-VD$_3$:

MS (m/e): 419 (M$^+$), 401 (M$^+$—H$_2$O), and 383 (M$^+$—2H$_2$O).

UV (EtOH): λmax 265 nm.

Tritium substitution reaction was also performed to obtain the following compound substituted with tritium atom.

1α,25 (OH)$_2$-(6, 19, 19-T)-VD$_3$:

MS (m/e): 422 (M$^+$), 404 (M$^+$—H$_2$O), and 386 (M$^+$—2H$_2$O).

UV (EtOH): λmax 265 nm.

EXAMPLE 4

24R, 25-(OH)$_2$-VD$_3$ labelled on the side chain and 24R, 25-(OH)$_2$-VD$_3$ labelled on the skeleton were compared for the stability of their labelled portion in a living body.

Each 100 μCi of (23, 24-T)-24R, 25-(OH)$_2$-VD$_3$ [compound (I''')] and (6, 19, 19-T)-24R,25-(OH)$_2$-VD$_3$ [compound (I″)] was orally administered to dogs of 7 kg body weight each and bred on normal diet. Samples of their blood and urine were taken time to time and their radioactivities were measured. The results were shown in Table 1.

The radioactivity in urine taken from the dog administered with the compound (I‴) increased in a short period of time and the most part of the radioactivity was derived from $T_2O$ showing that the side chain having tritium atom (T) was split from the skeleton. On the other hand, this phenomenon was not observed with the urine sample taken from the dog administered with the compound (I″).

TABLE

Time Course Change of Radioactivity in The Urine (%)

| | Period of Sampling (Hour) | | |
|---|---|---|---|
| Compound | 0 to 24 | 24 to 48 | 48 to 72 |
| I‴ | 0.29 | — | 0.17 |
| I″ | trace | trace | trace |

What is claimed is:

1. A vitamin $D_3$ derivative represented by the formula (I):

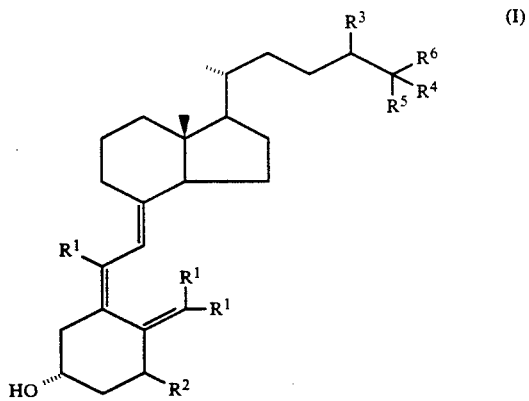

wherein $R^1$ represents a deuterium atom or a tritium atom; $R^2$, $R^3$ and $R^4$ independently represent a hydrogen atom or a hydroxy group, provided that at least one of $R^2$, $R^3$ and $R^4$ represents a hydroxy group; and $R^5$ and $R^6$ independently represent a methyl group, a hydroxymethyl group or a trifluorocarbon group.

2. The vitamin $D_3$ derivative according to claim 1, wherein $R^1$ represents a deuterium atom only or a tritium atom only, $R^2$ represents a hydrogen atom, $R^3$ and $R^4$ represent a hydroxy group and $R^5$ and $R^6$ represent a methyl group.

3. The Vitamin $D_3$ derivative according to claim 2, wherein $R^3$ is in an R-arrangement.

4. The vitamin $D_3$ derivative according to claim 1, wherein $R^1$ represents a deuterium atom or a tritium atom, $R^2$ represents a hydroxy group, $R^3$ represents a hydrogen atom, $R^4$ represents a hydroxy group, $R^5$ and $R^6$ represent a methyl group.

5. The vitamin $D_3$ derivative according to claim 1, wherein $R^1$ represents a deuterium atom or a tritium atom, $R^2$ and $R^3$ represent a hydrogen atom, $R^4$ represents a hydroxy group and $R^5$ represents a methyl group and $R^6$ represents a hydroxymethyl group.

* * * * *